United States Patent
Ensign et al.

(10) Patent No.: US 8,152,838 B2
(45) Date of Patent: Apr. 10, 2012

(54) ORTHOPEDIC PLATE SYSTEM AND METHOD FOR USING THE SAME

(75) Inventors: Michael D. Ensign, Salt Lake City, UT (US); David T. Hawkes, Pleasant Grove, UT (US)

(73) Assignee: Alphatec Spine, Inc., Carlsbad, CA (US)

( * ) Notice: Subject to any disclaimer, the term of this patent is extended or adjusted under 35 U.S.C. 154(b) by 771 days.

(21) Appl. No.: 11/357,692

(22) Filed: Feb. 17, 2006

(65) Prior Publication Data
US 2006/0200147 A1    Sep. 7, 2006

Related U.S. Application Data

(60) Provisional application No. 60/654,776, filed on Feb. 18, 2005.

(51) Int. Cl.
*A61B 17/80* (2006.01)
(52) U.S. Cl. ......... 606/289; 606/288; 606/290; 606/280
(58) Field of Classification Search .................... 606/69, 606/70–71, 280–299; 411/11–112, 354, 411/304, 356, 358, 360, 371.1–371.2, 362–365, 411/271, 325, 140, 357
See application file for complete search history.

(56) References Cited

U.S. PATENT DOCUMENTS

| | | | |
|---|---|---|---|
| 5,269,784 A | 12/1993 | Mast | |
| 5,364,399 A | 11/1994 | Lowery et al. | |
| 5,601,553 A | 2/1997 | Trebing et al. | |
| 5,681,311 A | 10/1997 | Foley et al. | |
| 5,713,900 A | 2/1998 | Benzel et al. | |
| 5,725,588 A | 3/1998 | Errico et al. | |
| 5,902,303 A * | 5/1999 | Eckhof et al. | 606/60 |
| 6,030,389 A * | 2/2000 | Wagner et al. | 606/71 |
| 6,575,975 B2 * | 6/2003 | Brace et al. | 606/86 B |
| 6,602,255 B1 | 8/2003 | Campbell et al. | |
| 6,613,053 B1 * | 9/2003 | Collins et al. | 606/69 |
| 7,033,121 B2 * | 4/2006 | Kirchen | 411/48 |
| 2004/0087951 A1 * | 5/2004 | Khalili | 606/69 |
| 2004/0127899 A1 * | 7/2004 | Konieczynski et al. | 606/69 |
| 2005/0049593 A1 | 3/2005 | Duong et al. | |
| 2005/0149027 A1 * | 7/2005 | Campbell et al. | 606/70 |

* cited by examiner

*Primary Examiner* — Thomas C. Barrett
*Assistant Examiner* — Matthew Lawson
(74) *Attorney, Agent, or Firm* — Michael R. Shevlin

(57) ABSTRACT

An orthopedic bone fixation device for stabilizing a plurality of bone segments includes a bone plate and a screw assembly. The bone plate includes a body defining at least one thru-bore, wherein the thru-bore is defined to include a central cavity, the central cavity having a middle diameter, an entry diameter, and an exit diameter, the middle diameter being larger than both the entry diameter and the exit diameter. Further, the screw assembly is configured to be coupled to the bone plate, wherein the screw assembly includes a bone screw having a head section, a thread section, and a central bore, an expandable ring coupled to the head section, and a pin at least partially disposed in the central bore, wherein the pin includes a varying outer profile that engages the expandable ring to vary an outer diameter of the expandable ring to lock the screw assembly in the thru-bore.

24 Claims, 11 Drawing Sheets

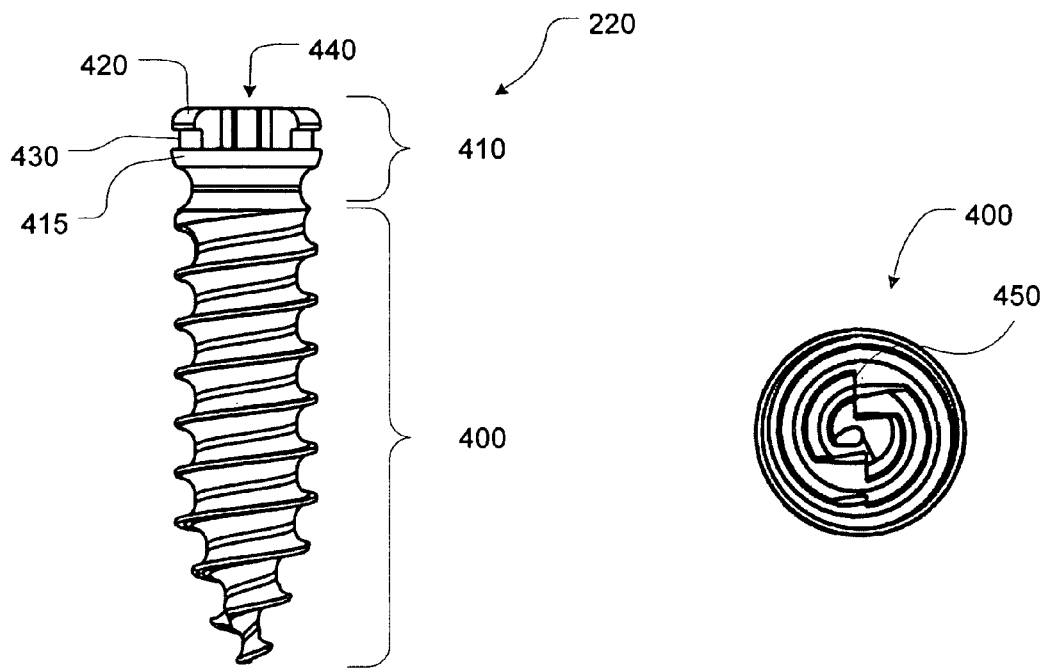
Fig. 4A
Fig. 4B
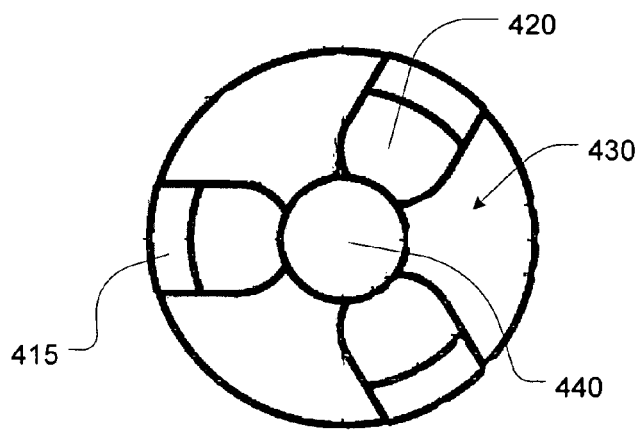
Fig. 4C
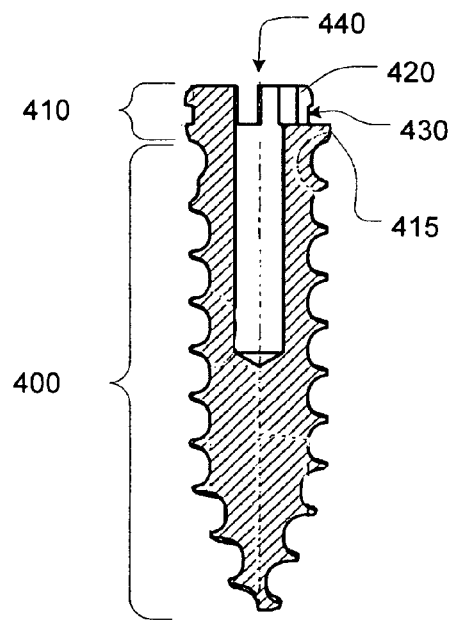
Fig. 4D

ORTHOPEDIC PLATE SYSTEM AND METHOD FOR USING THE SAME

RELATED APPLICATIONS

This application claims the benefit under 35 U.S.C. §119 (e) of U.S. Provisional Patent Application No. 60/654,776 filed Feb. 18, 2005 titled "Cervical Plate." The provisional application is incorporated herein by reference in its entirety.

FIELD

The present system and method relate to bone fixation devices. More particularly, the present system and method provide for an orthopedic system including a plate, a screw system, and a complete system including both the plate and screw system.

BACKGROUND

In the treatment of various spinal conditions, including the treatment of fractures, tumors and degenerative conditions, it is necessary to secure and stabilize the anterior column of the spine following removal of a vertebral body or part. Various devices for internal fixation of bone segments in the human or animal body are known in the art.

Following such removal made using a thoracotomy, thoracoabdominal or retroperitoneal approach, the normal anatomy is reconstructed using tricortical iliac crest or fibular strut grafts. Not only are removals performed on the thoracic spine, as is the case for the above procedures, but also the cervical spine. Once bone matter is removed, it is then necessary to secure and stabilize the graft, desirably in such a manner as to permit rapid mobilization of the patient. Such objectives can be accomplished by a bone plate. However, to accomplish this service in the optimum manner, it is necessary that the plate be reasonably congruent with the bone to which it is applied, that it have as low a profile as possible, that it be firmly secured to the spinal column so that it is not torn out when the patient places weight and stress upon it and that it be capable of placement and fixation in a manner that is convenient for the surgeon.

In this context it is necessary to secure the plate to the spinal body and also, in some cases, to the graft. Conventionally, such attachment would be by the use of screws driven through screw holes in the plate into the bone. However, when stabilizing the position of cervical vertebrae, the plate is designed to lie near and posterior to the esophagus of the patient. Due to its relative location to the esophagus and other connective tissue, if the screw securing the plate to the cervical spine backs out, the screw could irritate or even pierce the esophagus, resulting in pain, infection, and/or possible death of the patient. Consequently, anti-back out mechanisms are desired in the orthopedic plate industry.

SUMMARY

According to one exemplary embodiment, an orthopedic bone fixation device for stabilizing a plurality of bone segments includes a bone plate and a screw assembly. The bone plate includes a body defining at least one thru-bore, wherein the thru-bore is defined to include a central cavity, the central cavity having a middle diameter, an entry diameter, and an exit diameter, the middle diameter being larger than both the entry diameter and the exit diameter. Further, the screw assembly is configured to be coupled to the bone plate, wherein the screw assembly includes a bone screw having a head section, a thread section, and a central bore, an expandable ring coupled to the head section, and a pin at least partially disposed in the central bore, wherein the pin includes a varying outer profile that engages the expandable ring to vary an outer diameter of the expandable ring to lock the screw assembly in the thru-bore.

BRIEF DESCRIPTION OF THE DRAWINGS

The accompanying drawings illustrate various exemplary embodiments of the present system and method and are a part of the specification. Together with the following description, the drawings demonstrate and explain the principles of the present system and method. The illustrated embodiments are examples of the present system and method and do not limit the scope thereof.

FIGS. 4A-4D are respectively a side, a bottom, a top, and a cross-sectional view of a bone screw, according to one exemplary embodiment.

Figure 1:
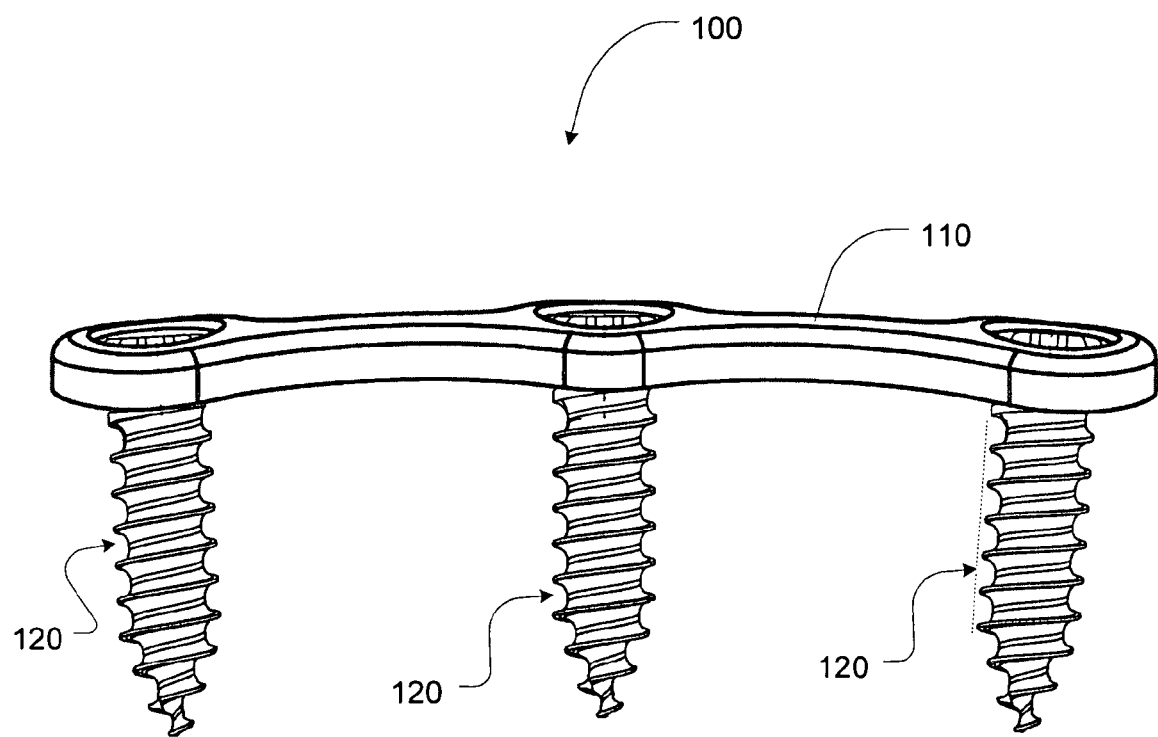
FIG. 1 is a side view of an assembled cervical plate system, according to one exemplary embodiment.

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings. Throughout the drawings, identical reference numbers designate similar but not necessarily identical elements.

DETAILED DESCRIPTION

The present specification describes a system and a method for coupling an orthopedic plate to one or more bones while preventing back-out of the fastener. Further, according to one exemplary embodiment, the present specification describes the structure of an orthopedic plate system that prevents back-out of a screw while positionally fixing bone segments. Further details of the present exemplary system and method will be provided below.

By way of example, orthopedic plate systems may be used in the treatment of various spinal conditions. As mentioned, when applied to stabilize the position of cervical vertebrae, the plate portion of the orthopedic plate system is designed to lie near and posterior to the esophagus of the patient. Due to its relative location to the esophagus and other connective tissue, the top surface of the plate portion may be smooth and free of sharp corners to prevent irritation or piercing of the esophagus and surrounding tissue. Further, in order to prevent irritation and/or piercing, any connection hardware that is used to couple the plate portion to the cervical vertebrae should remain below or even with the top surface of the plate portion.

If the screw or other fastener securing the plate portion to the cervical spine backs out or otherwise protrudes above the top surface of the plate portion, the screw could irritate or even pierce the esophagus, resulting in pain, infection, and/or possible death of the patient. Consequently, the present exemplary system and method provide an orthopedic plate system including a bone plate with thru-bores having varying diameters, with the larger diameter being constrained on the top and the bottom by smaller bore diameters. Further, a screw system is described below that, when assembled, is configured to leverage the varying bore diameter of the thru-bores formed in the bone plate to prevent the screw system from backing out.

Moreover, the present exemplary system and method provides anti-back out protection with a minimal engagement surface on the bone plate. Consequently, the profile size of the bone plate, when compared to traditional orthopedic plate systems, is reduced. This reduction in profile size adds comfort to the patient by reducing the likelihood that difficulty in swallowing will develop due to the presence of the orthopedic plate system.

In the following description, certain specific details are set forth in order to provide a thorough understanding of various embodiments of the present orthopedic plate system and method. However, one skilled in the relevant art will recognize that the present exemplary system and method may be practiced without one or more of these specific details, or with other methods, components, materials, etc. In other instances, well-known structures associated with orthopedic plate systems have not been shown or described in detail to avoid unnecessarily obscuring descriptions of the present exemplary embodiments.

As used in the present specification, and in the appended claims, the term "ring" or "expansion ring" shall not be interpreted as necessitating a circular cross section. Rather, as used herein and in the appended claims, the term "ring" or "expansion ring" may include any object having a substantially closed periphery regardless of the cross-sectional profile. The term "ring" shall include objects having flat sided profiles, curvilinear profiles, and/or profiles defined by a varying radius.

Additionally the term "pin" shall be interpreted broadly to include any elongate member, and is not limited to cylindrical elongate members. Rather, as used herein and in the appended claims, the term "pin" shall apply to elongate members having a circular, a quadratic, and/or non-symmetric cross-sectional profile.

Unless the context requires otherwise, throughout the specification and claims which follow, the word "comprise" and variations thereof, such as, "comprises" and "comprising" are to be construed in an open, inclusive sense, that is as "including, but not limited to."

Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular features, structures, or characteristics may be combined in any suitable manner in one or more embodiments.

Exemplary Structure

FIG. 1 illustrates an assembled cervical plate system (100), according to one exemplary embodiment. As illustrated, the exemplary cervical plate system (100) includes a number of components including, but in no way limited to, a bone plate (110) and at least one screw assembly (120) coupled to the bone plate (110). According to the exemplary embodiment illustrated in FIG. 1, the screw assemblies (120) are configured to be securely coupled to a patient's bone(s) while securely coupling to the bone plate (110) to provide structural and positional stability while preventing issues with the screw assembly backing out. Further, as illustrated in FIG. 1, the exemplary cervical plate system (100), when assembled, maintains the highest point of the screw assembly (120) below the highest surface of the bone plate (110).

Figure 2:
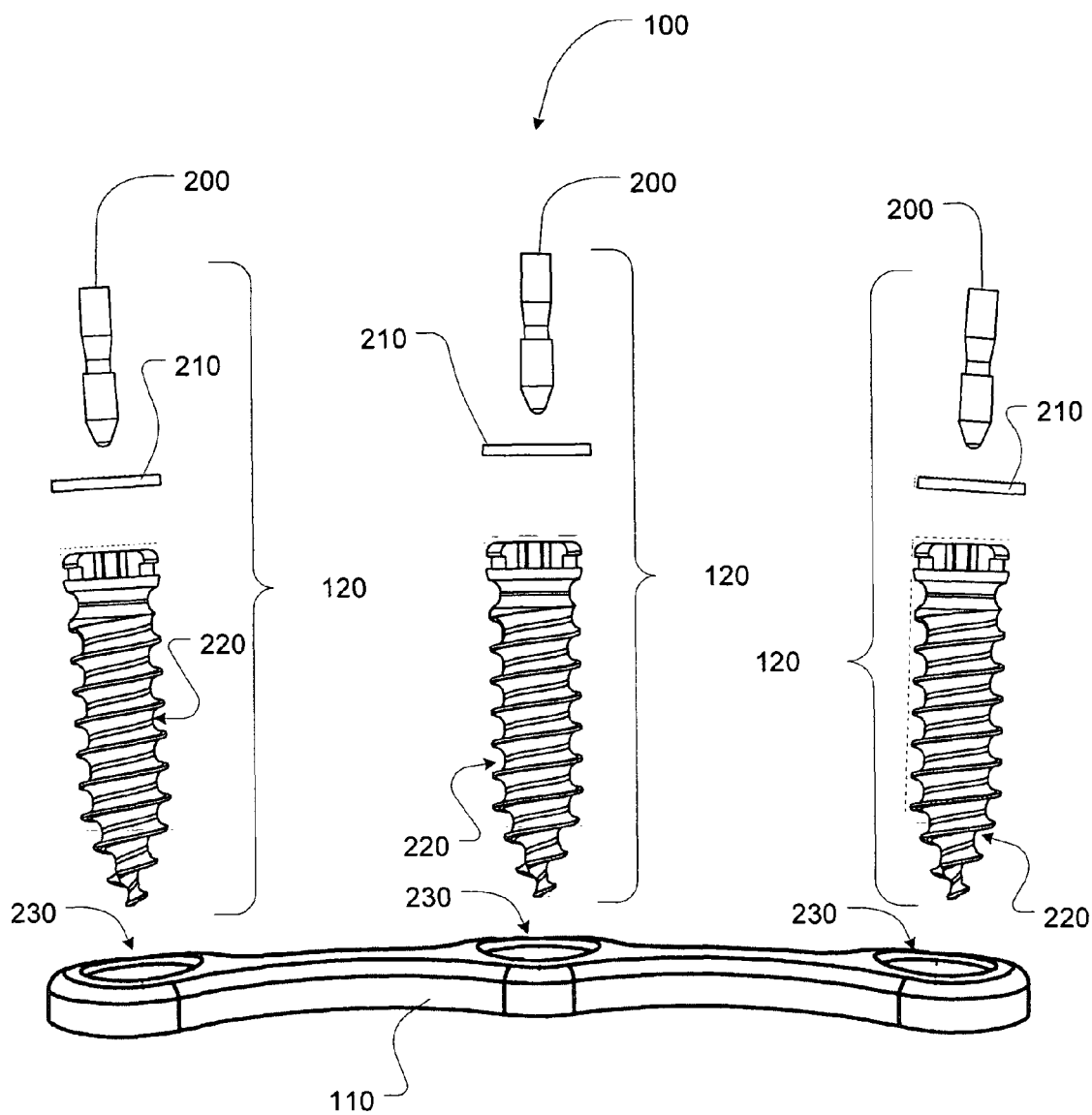
FIG. 2 is an exploded view illustrating the components of the screw assembly and bone plate of the exemplary embodiment illustrated in FIG. 1.

FIG. 2 is an exploded view of the exemplary cervical plate system (100) illustrating the components of the screw assembly (120). As shown in FIG. 2, the screw assembly (120) includes, but is in no way limited to, a lock pin (200), an expandable ring (210), and a bone screw (220). The various portions of the screw assembly (120) are selectively inserted into the thru bore(s) (230) formed in the exemplary bone plate (110). As mentioned, when fully engaged, the exemplary cervical plate system (100) is able to maintain a relatively low profile while providing structural support and preventing screw back out. A detailed description of each of the components of the exemplary cervical plate system (100) is provided below, followed by a description of their interaction during assembly.

Figure 3A:
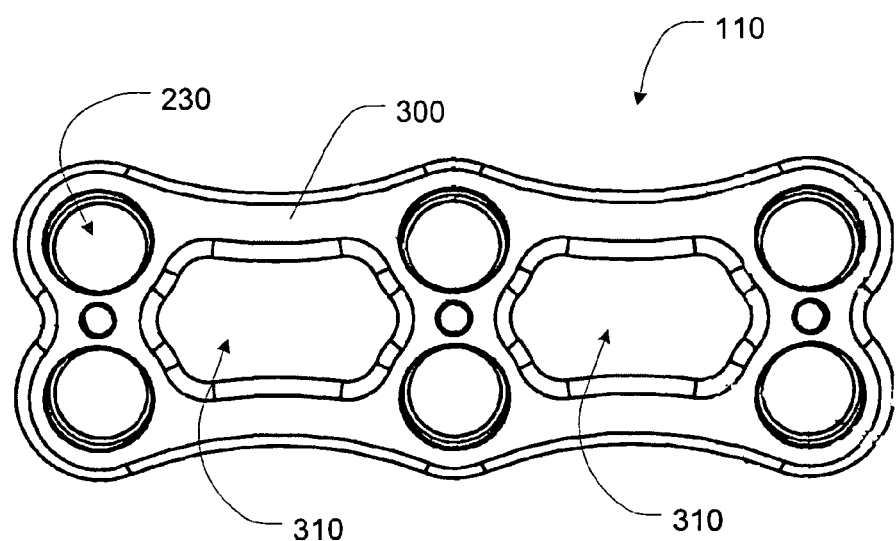
FIGS. 3A-3C are respectively top, side, and cross-sectional views of a bone plate, according to various exemplary embodiments.
Figure 3B:
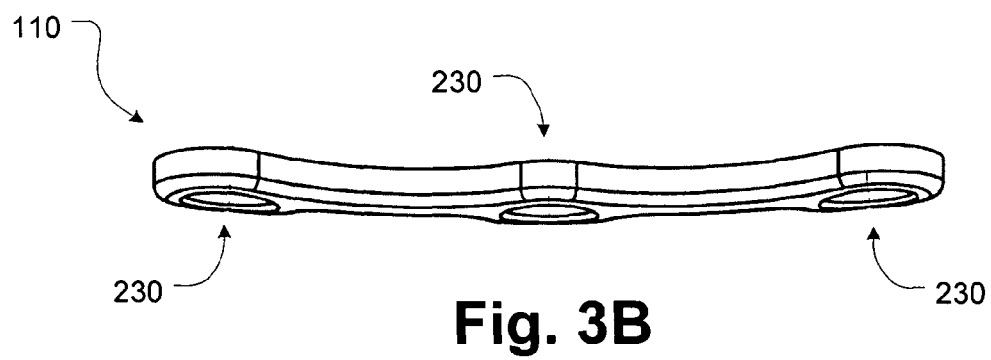
Figure 3C:
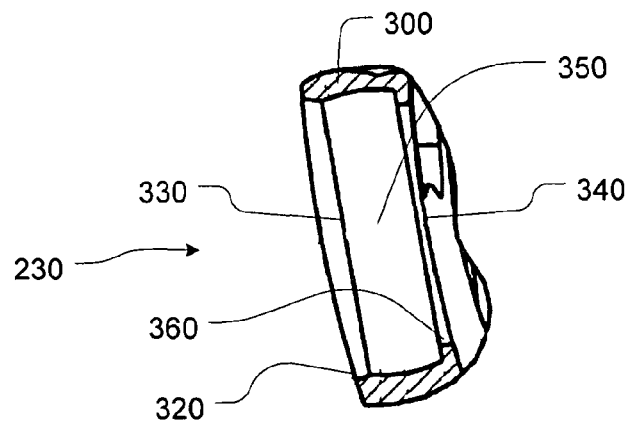

FIGS. 3A, 3B, and 3C illustrate various views of the bone plate (110), according to one exemplary embodiment. As shown, the bone plate generally includes a main plate body (300) having a number of material cut-out(s) (310) and thru-bore(s) (230) formed therein. As illustrated, the plate body (300) of the bone plate (110) is slightly curved to follow the shape of a spinal column and may be formed out of any number of biocompatible metals including, but in no way limited to, stainless steel, titanium, or a titanium alloy. Moreover, the construction of the plate body (300) may be made of non-metal materials including, but in no way limited to, carbon reinforced Polyetheretherketone (PEEK), and the like. Additionally, as illustrated in FIGS. 3A and 3B, the plate body (300) has a beveled rounded periphery to eliminate any sharp or abrupt edges that could potentially be damaging to surrounding tissue.

The material cut-out(s) (310) formed in the plate body (300) may serve a number of purposes. According to one exemplary embodiment, the material cut-out(s) (310) may be designed to eliminate superfluous material, thereby reducing the overall weight of the bone plate (110), while maintaining the desired structural integrity. Additionally, the various material cut-out(s) (310) may be configured to facilitate handling of the bone plate (110) during installation or removal with a tool such as, but in no way limited to, forceps. Further, the material cut-out(s) (310) may also provide functional access to tissue and/or bone located behind an installed bone plate (110) without necessitating removal of the plate.

FIG. 3C is a cross-sectional view detailing an exemplary varying profile of the thru-bore (230), according to one exemplary embodiment. As shown, a plurality of thru-bores (230) are formed in the plate body (300), six in the exemplary embodiment illustrated in FIG. 3A. A pair of thru-bores (230) are formed at each of the extreme ends and the center of the plate body (300), according to the exemplary embodiment illustrated in FIG. 3A. However, any number of thru-bore configurations may be employed in the plate body (300) to accomplish varying desired coupling points.

As illustrated in the cross-sectional view of FIG. 3C, each of the exemplary thru-bore(s) (230) include a reception chamfer (320) formed at the interface with the top surface of the plate body (300). The reception chamfer (320) of the exemplary thru bore(s) (230) facilitates reception of a screw assembly (120; FIG. 2) while eliminating the formation of a sharp or potentially damaging edge at the surface of the plate body (300).

Further, as shown, the thru-bore (230) includes a varying bore profile including a top reception diameter (330), a center cavity diameter (350), and an exit diameter (340) defined by a bore stop (360). According to one exemplary embodiment, described in further detail below, both the top reception diameter (330) and the exit diameter (340) of the exemplary thru-bore(s) (230) are smaller than the central cavity diameter (350). Due to the varying bore profile, a screw assembly (120; FIG. 2) having a selectively actuated expansion member may be inserted into the thru-bore(s) (230) and the expansion member actuated to approximately the diameter of the central cavity diameter (350). According to the present exemplary embodiment, expanding the expansion member to approximately the diameter of the central cavity diameter (350) will create an interference fit between the plate body (300) and the expansion member in all directions, thereby eliminating any degrees of freedom the screw assembly (120; FIG. 2) may have relative to the plate body (300). According to another exemplary embodiment, the expansion member may be actuated to a size slightly greater than that of the reception diameter (330) yet less than the central cavity diameter (350). According to this exemplary embodiment, the size of the expansion member will prevent exit of the screw assembly (120; FIG. 1) from the thru-bore (320) while allowing for movement of the screw head within the thru-bore. This movement may be beneficial as an intermediate step when a surgeon is initially placing the bone plate.

Further, according to one exemplary embodiment, the bore stop protrusion (360) that defines the exit diameter (340) of the thru-bore (230) may cause the exit diameter to be smaller than the diameter of the head base (415; FIG. 4) of the screw assembly (120). Consequently, the screw assembly (120) may be inserted into a bone via the bone plate (110) until the head base (415; FIG. 4) is seated upon the bore stop (360). The incorporation of the bore stop provides for consistent insertion of the screw assembly (120) relative to the top surface of the bone plate (110). While the bore profile of the present exemplary thru-bore (230) is illustrated as having gradual changes in the internal diameter, abrupt or dramatic variations in profile of the thru-bore (230) may also define the thru-bore, according to one exemplary embodiment.

FIGS. 4A through 4D detail a number of elements of a bone screw (220), according to one exemplary embodiment. As illustrated, the bone screw (220) includes features generally classified as a thread portion (400) and a head portion (410). According to one exemplary embodiment, the thread portion (400) of the bone screw (220) is configured to be affixed to the bone of a patient during spine surgery. Particularly, as shown, the thread portion (400) of the exemplary bone screw (220) may include a self-tapping leading edge (450), as is best shown in FIG. 4B. According to this exemplary embodiment, the incorporation of a self-tapping leading edge in the thread portion (400) of the bone screw (220) provides the bone screw with the ability to remove bone material as it is being inserted, eliminating a step of a surgeon drilling a pilot hole prior to insertion of the bone screw.

The head portion (410) of the bone screw (220) includes a number of functional features including, but in no way limited to, a plurality of driving features (420) formed on a head base (415), a ring channel (430) formed in a side of the driving features, and a pin bore (440) extending from the center of the head portion into the center of the thread portion (400). According to the present exemplary embodiment, the head portion (410) of the bone screw (410) transitions from the thread portion (400) with the head base (415). According to one exemplary embodiment, the outer diameter of the head base (415) is larger than the outer diameter of any section of the thread portion (400). By forming the head base (415) larger than the thread portion (400) of the bone screw (220), the thread portion of the bone screw may pass through an appropriately sized thru-bore (230; FIG. 2) substantially corresponding in size with the thread portion while preventing the head base from passing there through. This configuration allows for consistent insertion depth of the bone screw (220) into a desired thru-bore (230; FIG. 2).

A number of protrusions in the form of driving features (420) are formed extending upwardly from the head base (415), according to one exemplary embodiment. As illustrated in FIGS. 4A and 4C, the shown embodiment includes three protrusions acting as driving features (420). However, any number of driving features (420) may be formed on the head base (415), according to the teachings of the present exemplary system and method. According to one exemplary embodiment, at least the upper portion of the driving features may be engaged by a corresponding driving feature during installation. According to this exemplary embodiment, the corresponding driving feature (not shown) may engage the driving features (420) and impart a rotational force thereon, driving the thread portion (400) of the bone screw (220) into a desired bone.

As illustrated in FIGS. 4A and 4D, an annular groove is formed in the driving features (420) to form a ring channel (430) around the head portion (410) just above the head base (415). According to one exemplary embodiment, the ring channel (430) formed in the driving features (420) of the present exemplary bone screw (220) is sufficiently deep to receive and house an expandable ring (210; FIG. 2) in a relaxed state and retain the expandable ring when driven open to retain the screw assembly (120; FIG. 1) in a thru-bore (230; FIG. 2).

A pin bore (440) is also formed in the exemplary bone screw (220), as is best illustrated in FIG. 4D. According to one exemplary embodiment, the pin bore (440) is formed concentric with the axis of the bone screw (220) and has a diameter substantially similar to the diameter of the lock pin (200; FIG. 2). As shown in FIG. 4D, the pin bore (440) may also correspond in height with the height of a lock pin (200; FIG. 2) to assure the lock pin may be fully inserted into the pin bore (440) during operation.

Alternatively, the pin bore (440) formed in the exemplary bone screw (220) may be formed with a height that well exceeds the height of a lock pin (200). According to this alternative embodiment, the bone screw (220) may have a pin bore (440) that extends through the entire screw height.

According to this exemplary embodiment, the extended pin bore (440) not only allows for a lock pin (200) to be fully engaged to selectively expand an expandable ring (210), but also allows for a lock pin to be extended beyond the expandable ring into the pin bore (440), thereby facilitating a release of the expandable ring.

Figure 5A:
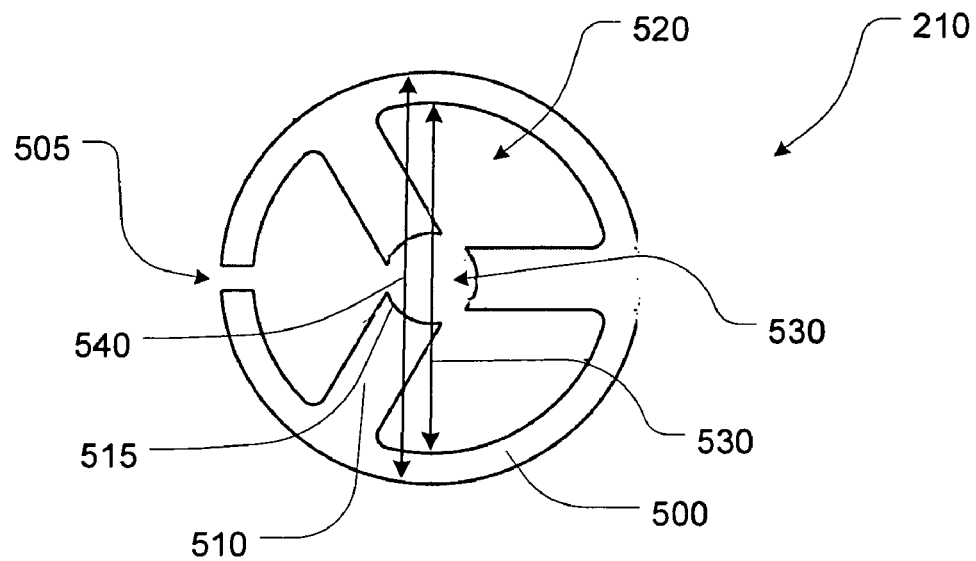
FIGS. 5A and 5B are respectively a top an a side view of an expandable ring configured to be mated with a bone screw, according to one exemplary embodiment.
Figure 5B:
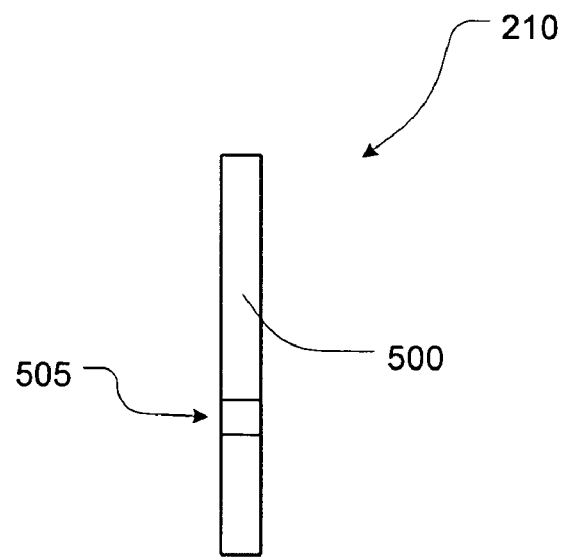

FIGS. 5A and 5B illustrate the expandable ring (210) of the screw assembly (210; FIG. 2), according to one exemplary embodiment. As shown in FIGS. 5A and 5B, the exemplary expandable ring is configured to mate with and be selectively expanded in the ring channel (430; FIG. 4A) of the bone screw (220). Specifically, the expandable ring (210) includes a substantially circular outer rib (500) having an expansion gap (505) formed therein. According to one exemplary embodiment, the expansion gap (505) is configured to facilitate the expansion and contraction of the expandable ring (210) without causing undue stresses on the member material. The width of the outer rib (500) is defined by the difference between the inner diameter (530) of the outer rib and the outer diameter (540) of the outer rib. According to one exemplary embodiment described in further detail below, the difference between the inner diameter (530) and the outer diameter (540) is such that the expandable ring (210) may be retained in the ring channel (430; FIG. 4A) of the bone screw (220; FIG. 2) in both an un-expanded state and an expanded state within a thru-bore (230; FIG. 2).

In addition to the expansion gap (505), the expandable ring (210) includes a number of expansion ribs (510) protruding from the outer rib (500) toward the center of the expandable ring. As shown, the expansion ribs (510) terminate in a lock pin engagement surface (515) and define a driving feature orifice (520) between each pair of adjacent expansion ribs and a pin orifice (530) between the lock pin engagement surfaces. According to one exemplary embodiment, the driving feature orifices (520) are configured to receive the driving features (420; FIG. 4C) formed on the head portion (410; FIG. 4A) of the bone screw (220; FIG. 2), during assembly. Additionally, the lock pin engagement surfaces (515) cause the pin orifice (530) to be concentrically aligned with the pin bore (440; FIG. 4D) when assembled. Consequently, the engagement surfaces are configured to receive a lock pin (200; FIG. 2) and translate any variations in the surface profile of the lock pin to the outer rib (500) as the lock pin is passed into the pin bore (440; FIG. 4D), thereby controlling the expansion and/or contraction of the outer rib (500).

Figure 6A:
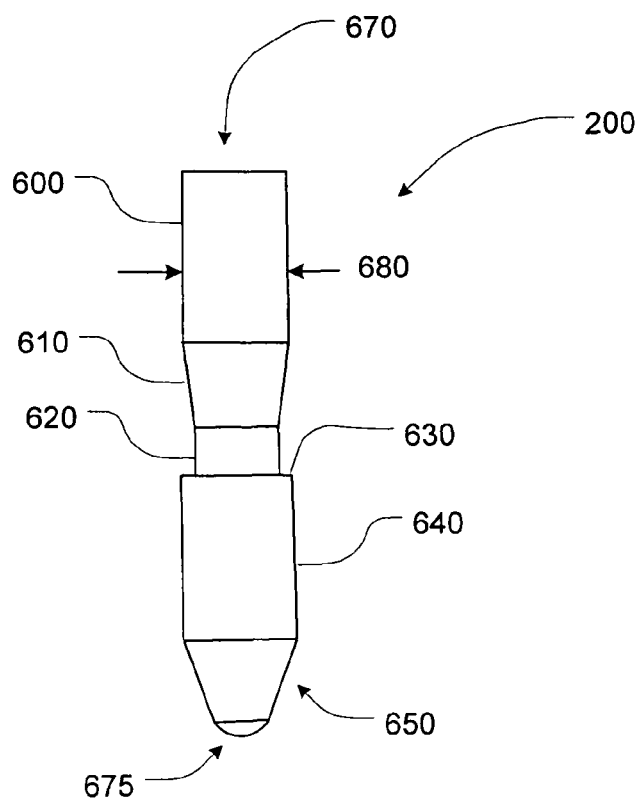
FIGS. 6A and 6B are a side view and a top view of a lock pin, according to one exemplary embodiment.
Figure 6B:
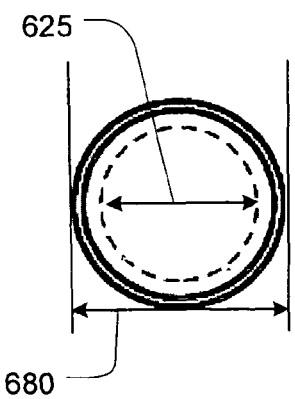

FIGS. 6A and 6B illustrate an exemplary lock pin (200) according to one exemplary embodiment. As shown, the exemplary lock pin (200) is a substantially cylindrical member having a proximal (670) and a distal end (675). Additionally, a number of cut outs and/or tapers are formed in the lock pin (200) to create a varying outer pin diameter (680). According to the exemplary embodiment illustrated in FIGS. 6A and 6B, the lock pin (200) includes an entry taper (650) formed on the distal end (675) thereof. The entry taper (650) is a graduated surface configured to facilitate initial alignment and engagement of the lock pin (200) with both the pin orifice (530; FIG. 5A) of the expandable ring (210; FIG. 5A) and the pin bore (440; FIG. 4D) of the bone screw (220; FIG. 4D).

Moving towards the proximal end (670) of the lock pin (200), the entry taper (650) leads to an entry body (640) having a substantially consistent outer pin diameter (680) configured to at least slightly expand the expandable ring (210) during assembly. The entry body (640) leads to a retention cut-out (630) portion (630) that defines a small diameter surface (620) of the lock pin (200). According to one exemplary embodiment, the small diameter surface (620) has a relaxed diameter (625) substantially corresponding to the pin orifice (530; FIG. 5A) in a relaxed or near relaxed expandable ring state. According to one exemplary embodiment, when the screw assembly (120; FIG. 2) is assembled, the expandable ring (210) engages the small diameter surface (620), allowing the expandable ring to remain in a relaxed state until fully engaged.

Continuing towards the proximal end (670) of the lock pin (200), a graduated expansion surface (610) extends from the small diameter surface (620), terminating in the lock surface (600) portion of the lock pin (200). During a locking step of the present exemplary system, the lock pin (200) is advanced in the pin bore (440; FIG. 4D) such that the lock pin engagement surfaces (515; FIG. 5A) of the expandable ring (210) engage the graduated expansion surface (610) and the lock surface (600) to expand the expandable ring to an appropriate diameter within the thru-bore (230; FIG. 2). According to one exemplary embodiment, the outer pin diameter (680) of the lock surface (600) is sufficient to expand the expandable ring (210; FIG. 2) to a desired friction inducing state, while still constraining the expandable ring in the ring channel (430; FIG. 4A) and without permanently deforming the expansion ring. Further detail of the function and operation of the exemplary cervical plate system (100) will be described below with reference to FIGS. 7-11.

Exemplary Method

Figure 7:
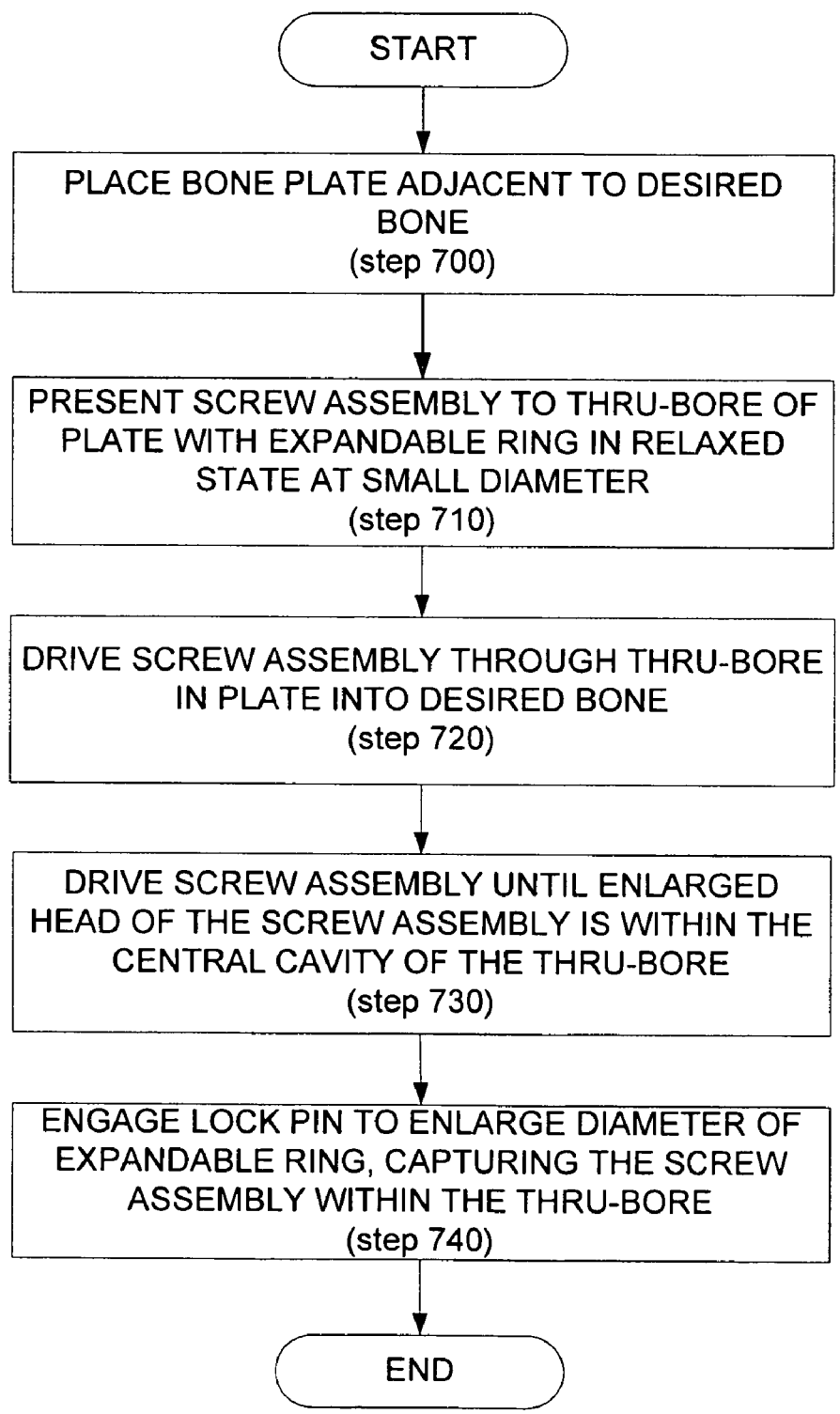
FIG. 7 is a flow chart illustrating a method of securing an orthopedic plate, according to one exemplary embodiment.

FIG. 7 illustrates a method for installing the exemplary cervical plate system (100; FIG. 1), according to one exemplary embodiment. As illustrated in FIG. 7, the present exemplary method for installing the cervical plate system (100; FIG. 1) includes placing the bone plate adjacent to one or more desired vertebral bones (step 700). Once the bone plate is appropriately positioned, the screw assembly may then be presented to a thru-bore of the bone plate with the expandable ring in a relaxed state at a small diameter (step 710). The screw assembly is then driven through the thru-bore in the bone plate into the desired vertebral bone (step 720) until the enlarged head of the screw assembly is within the central cavity of the thru-bore, seated on the bore stop (step 730). Once the screw assembly is correctly positioned, the lock pin may be translated to enlarge the diameter of the expandable ring, thereby capturing the screw assembly within the thru-bore (step 740). Further details of each step of the present exemplary method will be provided below with reference to FIGS. 8 through 11.

Figure 8:
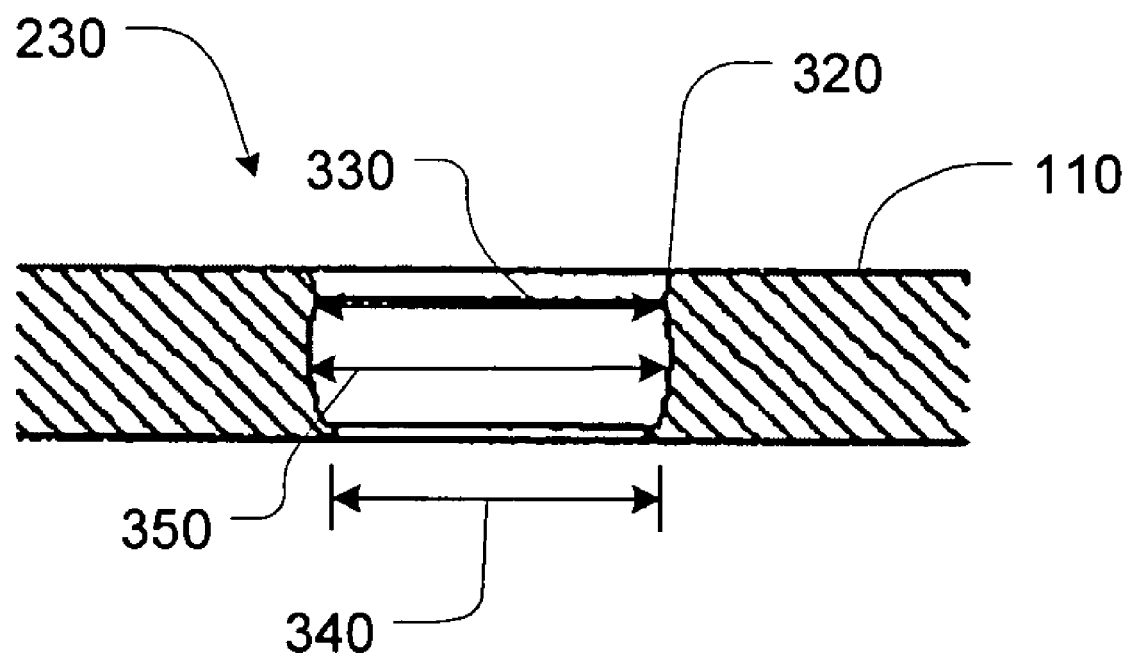
FIG. 8 is an enlarged cross-sectional view of a thru-bore of an orthopedic plate during installation, according to one exemplary embodiment.

As illustrated in FIG. 7, the first step of the exemplary method is to place the plate adjacent to a desired vertebral bone (step 700). The placement of the bone plate (110; FIG. 1) relative to a vertebral bone in a patient may be pre-operatively determined based on a pre-operative examination of the patient's spinal system using non-invasive imaging techniques known in the art, such as x-ray imaging, magnetic resonance imaging (MRI), and/or fluoroscopy imaging, for example. Any additional preparation or work may be done on and around the desired vertebral bone prior to positionally orienting the bone plate. As illustrated in FIG. 8, the bone plate (110) is oriented such that the reception chamfer (320) is facing away from the desired bone, facilitating insertion of the present screw assembly.

Figure 9:
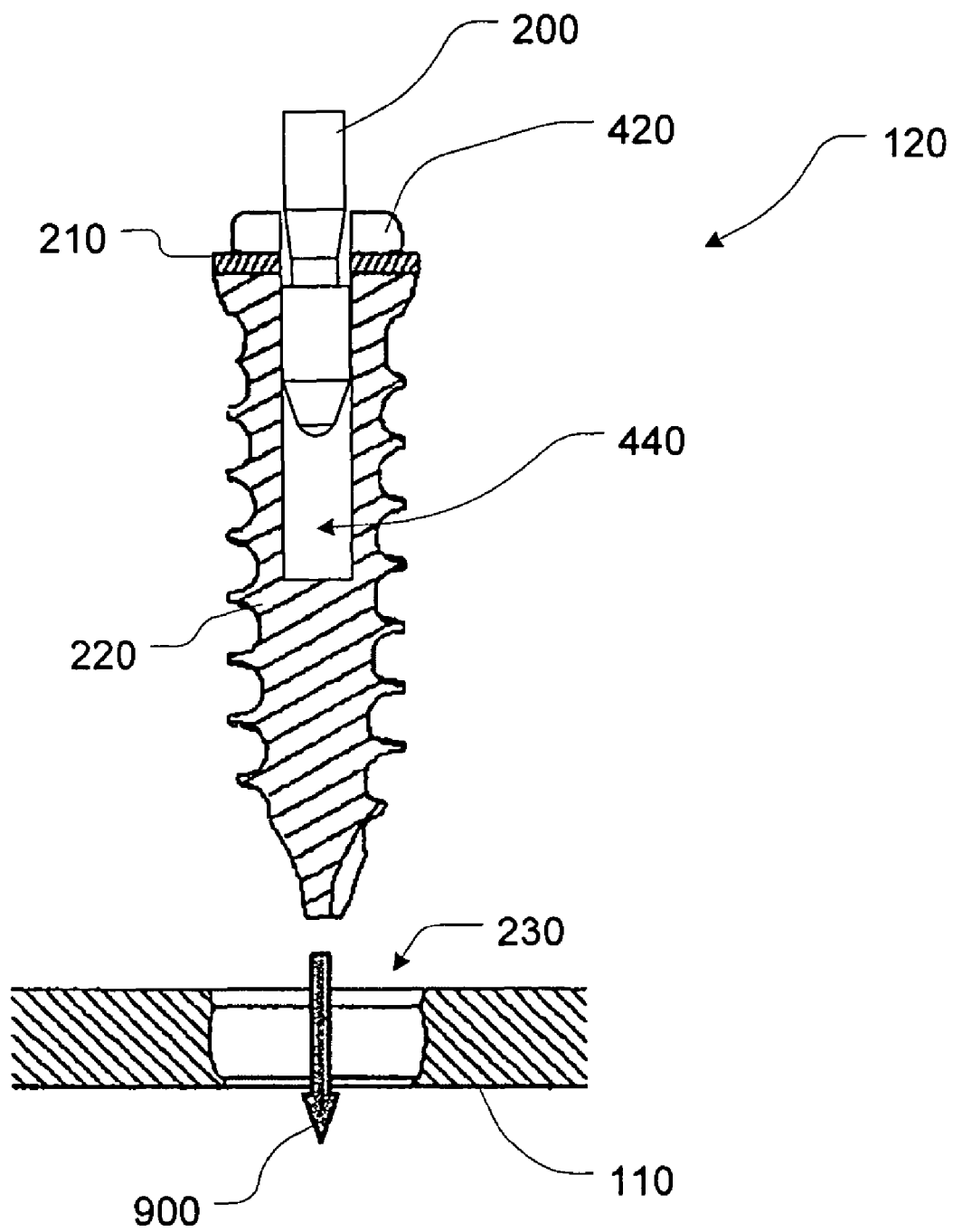
FIG. 9 is an enlarged cross-sectional view of a screw system being inserted into a thru-bore of an orthopedic plate, according to one exemplary embodiment.

With the bone plate appropriately positioned relative to a desired vertebral bone (step 700), the screw assembly may be presented to a thru-bore of the bone plate with the expandable ring in a relaxed state (step 710). As shown in FIG. 9, the screw assembly (120) may be delivered to the surgeon as a three piece assembly including the bone screw (220), the expandable ring (210), and the lock pin (200). According to the illustrated exemplary embodiment, when delivered to the surgeon, the lock pin (200) is undeployed and the expandable ring (210) is in a relaxed state. More specifically, according to one exemplary embodiment, the small diameter surface (620; FIG. 6A) of the lock pin (200) is engaged with the lock pin engagement surfaces (515; FIG. 5A) of the expandable ring (210). Maintaining the screw assembly (120) in this configuration during delivery and storage prevents any permanent deformation of the expandable ring (210) due to creep and other material phenomena.

When presented, the screw assembly (120) may then be driven through the thru-bore (230) in the bone plate (110) into a desired vertebral bone (step 720). As mentioned, the screw assembly may be driven into the desired vertebral bone by coupling a driving tool to the driving features (420) of the bone screw (220). Once mating, the driving tool may impart a rotational force on the head portion (410) of the bone screw (220). Consequently, the self-tapping thread portion (400; FIG. 4A) of the bone screw (220) will remove bone material as it advances into the desired bone. The screw assembly (120) may be partially driven initially if multiple screw assemblies (120) are to be inserted in a single bone plate (110) or if further work is to be done by a surgeon prior to final assembly.

Figure 10:
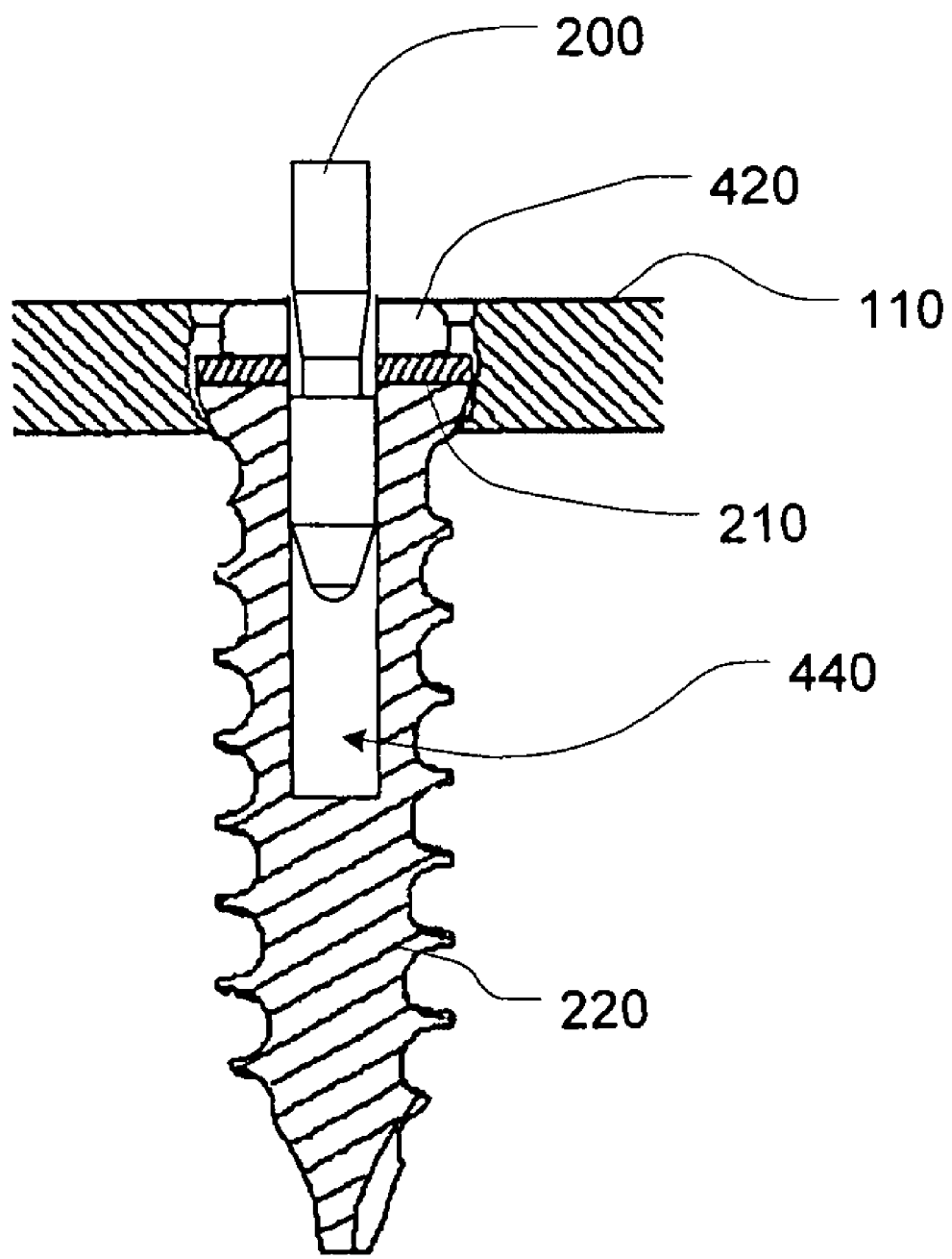
FIG. 10 is an enlarged cross-sectional view of a properly positioned screw system in a thru-bore of an orthopedic plate, in accordance with one exemplary embodiment.

The screw assembly (120) may be driven through the thru-bore (230) until the head portion (410) of the bone screw (220) is within the central cavity of the thru-bore (step 730). As mentioned previously, consistent seating of the screw assembly (120) in the thru-bore (230) may be accomplished by driving the bone screw (220) into the thru-bore (230) until the head base (415; FIG. 4A) of the bone screw seats upon the bore stop (360; FIG. 3C) within the thru-bore. FIG. 10 illustrates a screw assembly (120) seated in the thru-bore (230) as described above. As shown, by driving the bone screw (220) into the thru-bore (230) until the head base (415; FIG. 4A) of the bone screw seats upon the bore stop (360; FIG. 3C), the top surface of the head portion (410; FIG. 4A) is driven to or below the top surface of the bone plate (110).

Figure 11:
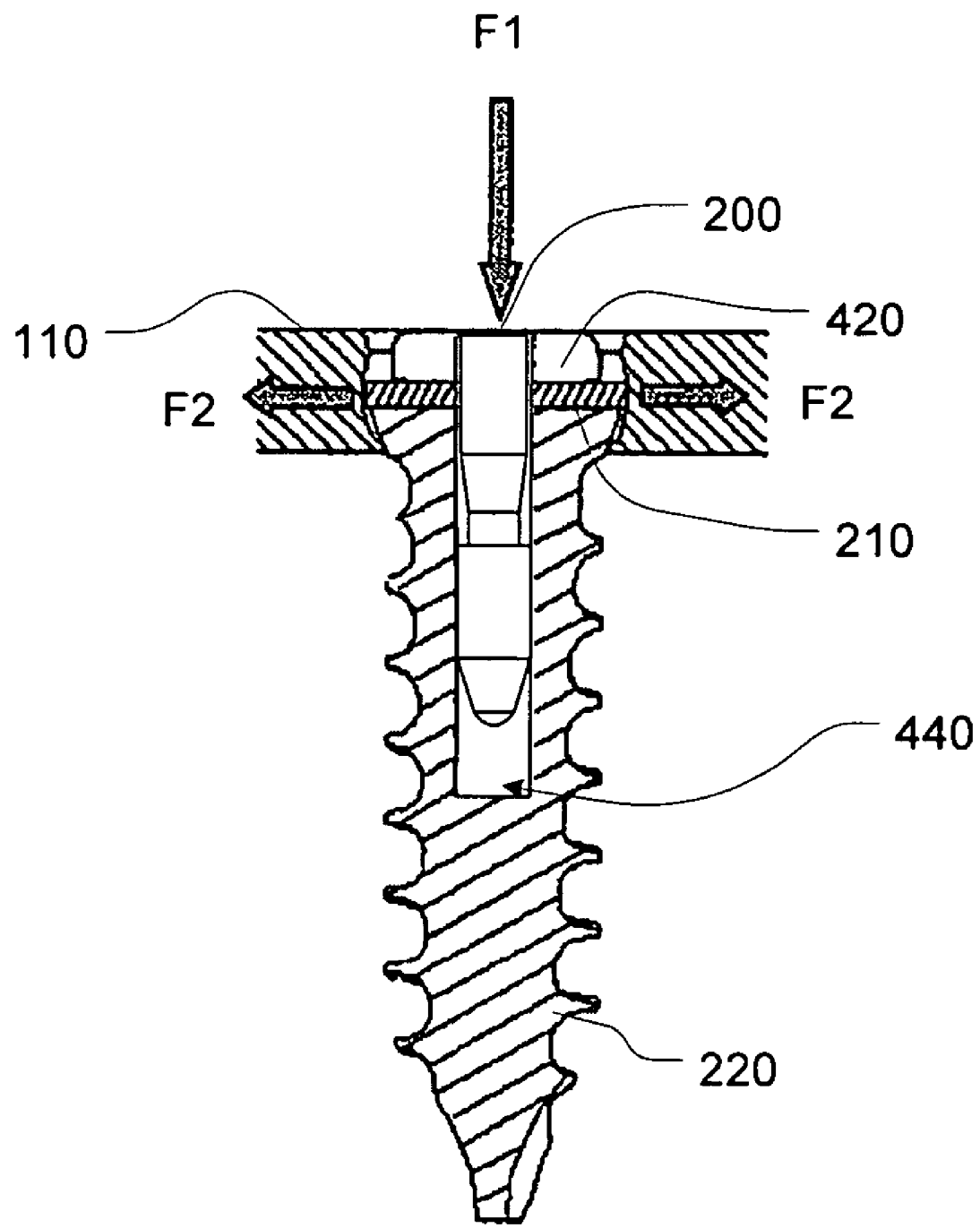
FIG. 11 is an enlarged cross-sectional view of a screw system securely coupled to a thru-bore of an orthopedic plate, according to one exemplary embodiment.

Once the screw assembly is correctly positioned in the thru-bore (230), the lock pin (200) may be engaged to enlarge the diameter of the expandable ring (210), capturing the screw within the thru-bore (step 740), as illustrated in FIG. 11. As mentioned previously, the lock pin (200) is engaged by applying a downward force (F1) to the lock pin (200). As the lock pin (200) is translated into the pin bore (440), the expansion ring (210) is acted upon by the varying profile of the lock pin. Specifically, the graduated expansion surface (610; FIG. 6A) of the lock pin (200) will impart an increasing force on the expansion ring (210) until the lock pin is fully engaged and the lock surface (600) is imparting a desired outward force upon the expansion ring. While an axial translation of the lock pin imparts a radial force on the expansion ring of the exemplary embodiment detailed herein, movement of the lock pin is in no way limited to an axial translation. Rather, by way of example, a lock pin having a non-circular cross-sectional profile, such as a triangle or other lobed profile, may be rotated within the pin bore (440) to impart a changing radial force on the expansion ring. In response to the increased outward force exerted by the lock surface (600) of the lock pin (200) upon the expansion ribs (540; FIG. 5A) of the expansion ring (210), the diameter of the expansion ring is enlarged about the head portion (410; FIG. 4A) of the bone screw assembly (120). The enlarging of the expansion ring (210) about the head portion (410; FIG. 4A) of the bone screw assembly (120) imparts an outward force (F2) from the expansion ring to the inner surface of the thru-bore (230). According to one exemplary embodiment, the outward force (F2) exerted by the expansion ring (210) to the thru-bore (230) creates a frictional fit that captures the bone screw (220) within the thru-bore of the bone plate. Further, as mentioned above, the outer diameter of the expansion ring (210) in its expanded state is larger than both the reception diameter (330; FIG. 3C) and the exit diameter (340; FIG. 3C) of the exemplary thru-bore (230). Consequently, the bone screw assembly (120) is prevented from backing out from, or further advancing in the thru-bore (230).

While the present exemplary orthopedic plate system (100; FIG. 1) has been described, for ease of explanation only, in the context of a cervical plate system, the present exemplary systems and methods may be applied to any number of orthopedic fixtures. Specifically, the present bone screw assembly (120) may be used to couple any number of orthopedic apparatuses to a desired bone, for any number of purposes, as long as the connecting orthopedic apparatus includes a thru-bore substantially conforming with the configurations described herein.

In conclusion, the present exemplary systems and methods provide for coupling an orthopedic plate to one or more bones while preventing back-out of the fastener. Particularly, the present exemplary system is configured to leverage the varying bore diameter of a thru-bore formed in the bone plate to prevent the screw system from backing out while utilizing a minimal engagement surface on the bone plate. Consequently, the profile size of the bone plate, when compared to traditional orthopedic plate systems, is reduced and the dangers associated with screw back-out are reduced. This reduction in profile size adds comfort to the patient by reducing the likelihood that difficulty in swallowing will develop due to the presence of the orthopedic plate system.

The preceding description has been presented only to illustrate and describe the present method and system. It is not intended to be exhaustive or to limit the present system and method to any precise form disclosed. Many modifications and variations are possible in light of the above teaching.

The foregoing embodiments were chosen and described in order to illustrate principles of the system and method as well as some practical applications. The preceding description enables others skilled in the art to utilize the method and system in various embodiments and with various modifications as are suited to the particular use contemplated. It is intended that the scope of the present exemplary system and method be defined by the following claims.

What is claimed is:

1. A Bone fixation system comprising:
    a bone screw including a head portion with an annular groove and a concentric pin bore extending into a threaded portion;
    an expandable ring including a substantially circular outer rib with an expansion gap retained within the annular groove and expansion ribs protruding from the outer rib toward the pin bore to form a pin orifice, wherein a diameter of the pin bore is greater than a diameter of the pin orifice;
    a pin slidably received in the pin bore with a varying outer profile that engages the expandable ring to selectively expand the expandable ring from an un-expanded state to an expanded state, wherein the pin includes a conical entry taper, the conical shape stopping at an entry body forming a cylindrical shape, the cylindrical shape becoming frusto-conical in a retention cut-out portion, and returning to the cylindrical shape in a gradual expansion portion; and a bone plate including a thru-bore with an entry diameter that receives the bone screw, wherein an outer diameter of the expandable ring is less than or equal to the entry diameter in the un-expanded state and greater than the entry diameter in the expanded state.

2. The system of claim 1, wherein the head portion further comprises a head base, protrusions in the form of driving features extending upwardly from the head base, and overhang members extending radially away from the driving features to form the annular groove therebetween.

3. The system of claim 1, wherein the annular groove retains the expandable ring in both the un-expanded state and the expanded state.

4. The system of claim 1, wherein each of the expansion ribs terminates in a pin engagement surface.

5. The system of claim 4, wherein each pin engagement surface contacts the pin and translates variations in the outer profile to the outer rib as the pin advances through the pin orifice and the pin bore.

6. The system of claim 2, wherein the expansion ribs define driving feature orifices between adjacent pairs of expansion ribs.

7. The system of claim 6, wherein the driving features extend through the driving feature orifices.

8. The system of claim 1, wherein the outer profile of the pin includes an entry taper, an entry body, a retention cut-out portion, a graduated expansion portion, and a lock surface that engage the expandable ring to selectively expand the expandable ring as the pin advances into the pin bore.

9. The system of claim 8, wherein the entry taper includes a graduated surface of varying diameter that is less than or equal to the diameter of the pin orifice to facilitate alignment of the pin with the pin bore.

10. The system of claim 9, wherein the entry taper leads to the entry body that includes a diameter greater than the diameter of the pin orifice and that expands the expandable ring to the expanded state.

11. The system of claim 10, wherein the entry body leads to the retention cut-out portion that includes a diameter less than or equal to the diameter of the pin orifice and that allows the expandable ring to return to the un-expanded state.

12. The system of claim 11, wherein the retention cut-out portion leads to the graduated expansion portion that includes an increasing diameter that gradually expands the expandable ring.

13. The system of claim 12, wherein the graduated expansion portion leads to the lock surface that includes a diameter greater than the diameter of the pin orifice and that expands the expandable ring to a desired friction inducing state within the thru-bore while constraining the expandable ring within the annular groove.

14. The system of claim 13, wherein the pin bore includes a height greater than a height of the pin such that the pin may be advanced past the pin orifice to allow the expandable ring to return to the un-expanded state.

15. A method for bone fixation comprising:
positioning a bone plate including a thru-bore with an entry diameter adjacent a bone;
inserting a bone screw into the thru-bore, wherein the bone screw includes a head portion with an annular groove and a concentric pin bore extending into a threaded portion,
wherein the annular groove retains an expandable ring;
positioning a substantially circular outer rib and expansion gap of the expandable ring within the annular groove such that expansion ribs protruding from the outer rib toward the pin bore from a pin orifice; and
sliding a pin into the pin bore, wherein a varying outer profile of the pin includes a conical entry taper, the conical shape stopping at an entry body forming a cylindrical shape, the cylindrical shape becoming frusto-conical in a retention cutout portion, and returning to the cylindrical shape in the graduated expansion portion, and wherein the varying outer profile engages the expandable ring to selectively expand the expandable ring from an un-expanded state to an expanded state, wherein an outer diameter of the expandable ring is less than or equal to the entry diameter in the un-expanded state and greater than the entry diameter in the expanded state.

16. The method of claim 15, further comprising retaining the expandable ring within the annular groove in both the expanded state and the un-expanded state.

17. The method of claim 15, further comprising translating variations in the outer profile of the pin via expansion ribs to an outer rib of the expandable ring as the pin advances through the pin bore.

18. The method of claim 15, further comprising aligning the pin with the pin bore using an entry taper of the pin, wherein the entry taper includes a graduated surface of varying diameter that is less than or equal to the diameter of the pin orifice.

19. The method of claim 18, further comprising advancing the pin until an entry body of the pin expands the expandable ring to the expanded state, wherein the entry body includes a diameter greater than the diameter of the pin orifice.

20. The method of claim 19, further comprising advancing the pin until a retention cut-out portion allows the expandable ring to return to the un-expanded state, wherein the retention cut-out portion includes a diameter less than or equal to the diameter of the pin orifice.

21. The method of claim 20, further comprising advancing the pin until a graduated expansion portion begins to expand the expandable ring, wherein the graduated expansion portion includes an increasing diameter greater than the diameter of the retention cut-out portion.

22. The method of claim 21, further comprising advancing the pin until a lock surface expands the expandable ring to a desired friction inducing state while constraining the expandable ring within the annular groove, wherein the lock surface includes a diameter greater than the diameter of the pin orifice.

23. The method of claim 22, further comprising advancing the pin past the pin orifice to allow the expandable ring to return to the un-expanded state, wherein the pin bore includes a height greater than a height of the pin.

24. A bone fixation system comprising:
a bone screw including a head portion with an annular groove and a concentric pin bore extending into a threaded portion;
an expandable ring including a substantially circular outer rib with an expansion gap retained within the annular groove and expansion ribs protruding from the outer rib toward the pin bore to form a pin orifice, wherein a diameter of the pin bore is greater than a diameter of the pin orifice;
a pin slidably received in the pin bore that engages the expandable ring to selectively expand the expandable ring from an un-expanded state to an expanded state, wherein the pin includes a conical entry taper, the conical shape stopping at an entry body forming a cylindrical shape, the cylindrical shape becoming frusto-conical in a retention cut-out portion, and returning to the cylindrical shape in a graduated expansion portion; and a bone plate including a thru-bore with an entry diameter that receives the bone screw, wherein an outer diameter of the expandable ring is less than or equal to the entry diameter in the un-expanded state and greater than the entry diameter in the expanded state, wherein a diameter of the pin bore is greater than a diameter of the pin orifice in the un-expanded state.

* * * * *